United States Patent
Berg et al.

(10) Patent No.: US 8,349,007 B2
(45) Date of Patent: Jan. 8, 2013

(54) BREAST IMPLANTS HAVING DRUG-ELUTING RESERVOIRS AND METHODS THEREFOR

(75) Inventors: Eric Peter Berg, Grapevine, TX (US); Anita Marie Falcon, Bedford, TX (US)

(73) Assignee: Mentor Worldwide LLC, Santa Barbara, CA (US)

( * ) Notice: Subject to any disclaimer, the term of this patent is extended or adjusted under 35 U.S.C. 154(b) by 181 days.

(21) Appl. No.: 12/648,435

(22) Filed: Dec. 29, 2009

(65) Prior Publication Data

US 2011/0160854 A1 Jun. 30, 2011

(51) Int. Cl.
*A61F 2/12* (2006.01)

(52) U.S. Cl. .......................................................... 623/8

(58) Field of Classification Search . 623/8; 604/288.02, 604/288.04, 892.1
See application file for complete search history.

(56) References Cited

U.S. PATENT DOCUMENTS

| | | | |
|---|---|---|---|
| 5,630,843 | A | 5/1997 | Rosenberg |
| 6,071,309 | A | 6/2000 | Knowlton |
| 6,605,116 | B2 | 8/2003 | Falcon et al. |
| 7,410,480 | B2 | 8/2008 | Muni et al. |

FOREIGN PATENT DOCUMENTS

FR 2690625 A1 11/1993

*Primary Examiner* — Bruce E Snow

(57) ABSTRACT

A breast implant includes an implant shell having an outer surface and defining a first fluid reservoir, and a porous membrane overlying the outer surface of the implant shell and defining a second fluid reservoir. The breast implant includes a filling tube having a first conduit in communication with the first reservoir and a second conduit in communication with the second reservoir. The breast implant includes an injection dome coupled with the filling tube and having a first fluid chamber in communication with the first conduit and a second fluid chamber in communication with the second conduit. The injection dome includes an upper end having an injection cover, a lower end including a support base, the first fluid chamber located adjacent the injection cover, the second fluid chamber located adjacent the support base, and a diaphragm dividing the first and second fluid chambers from one another.

4 Claims, 17 Drawing Sheets

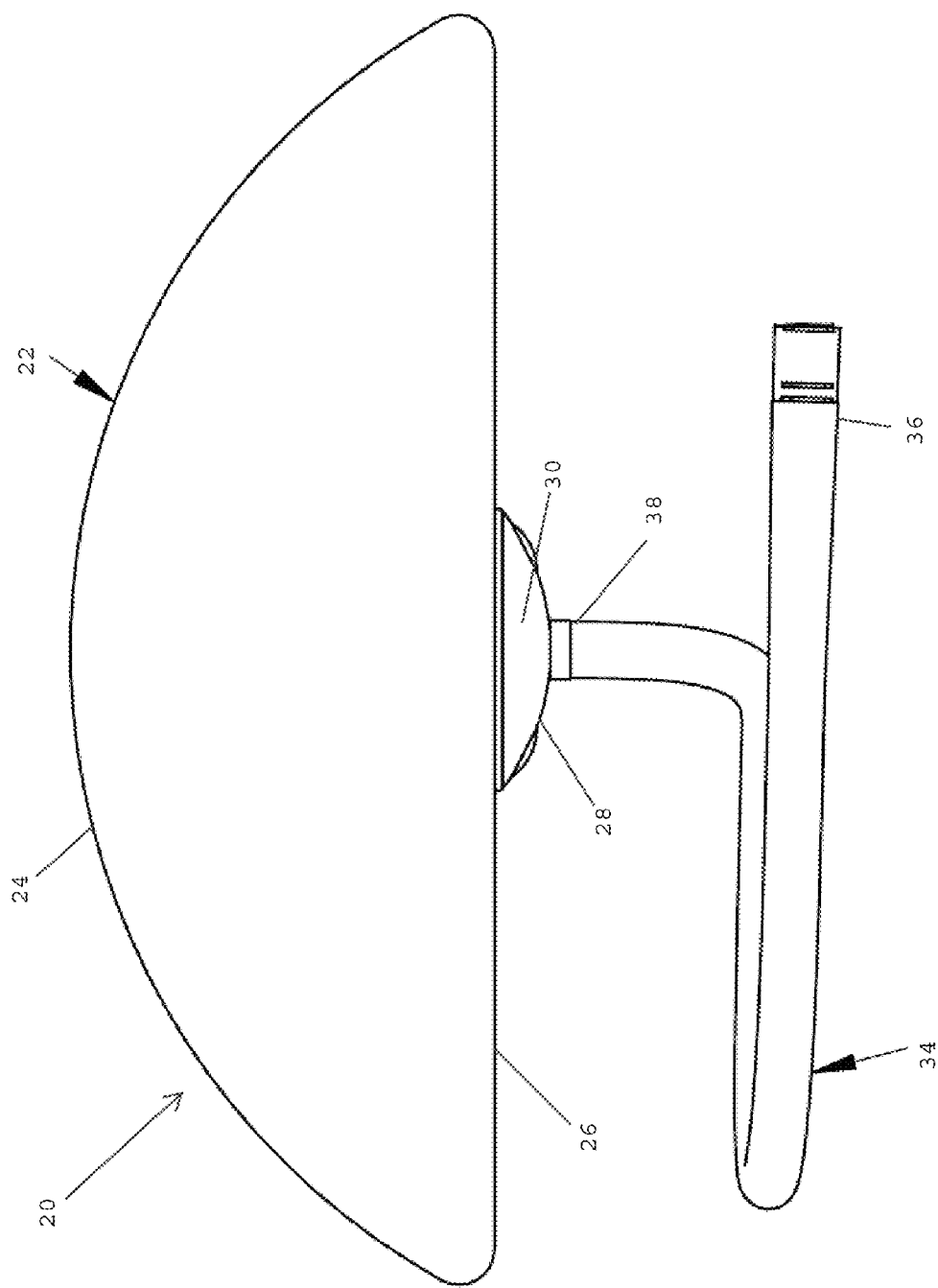

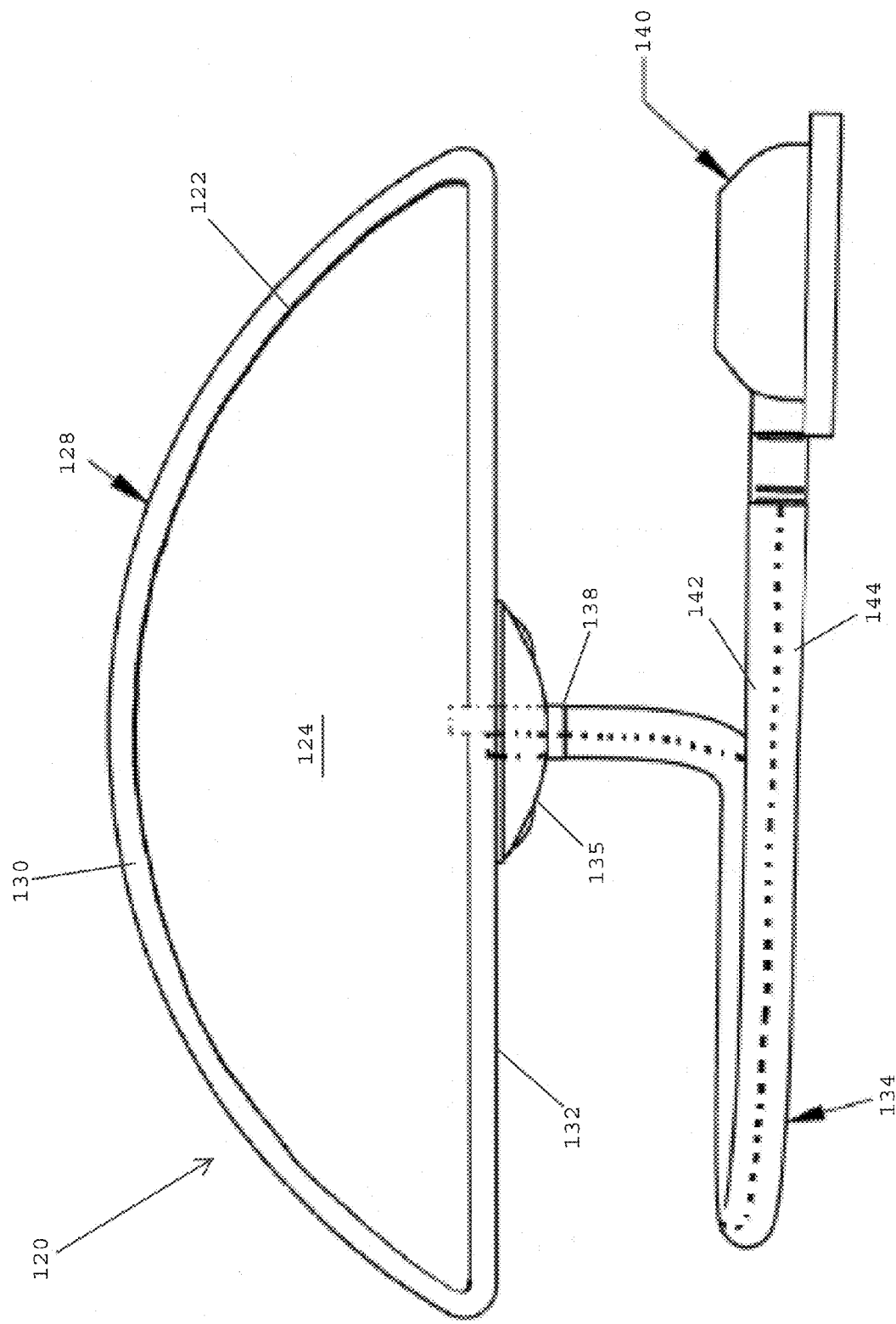

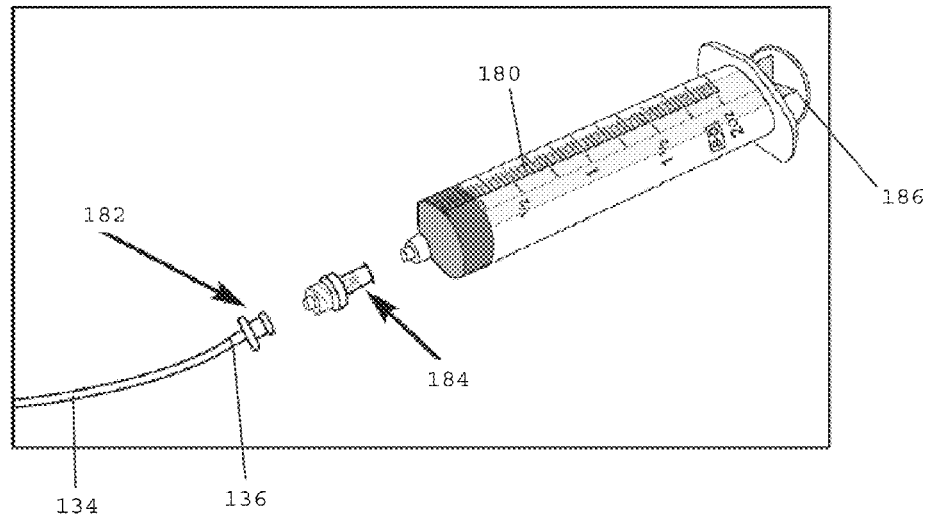
FIG. 4
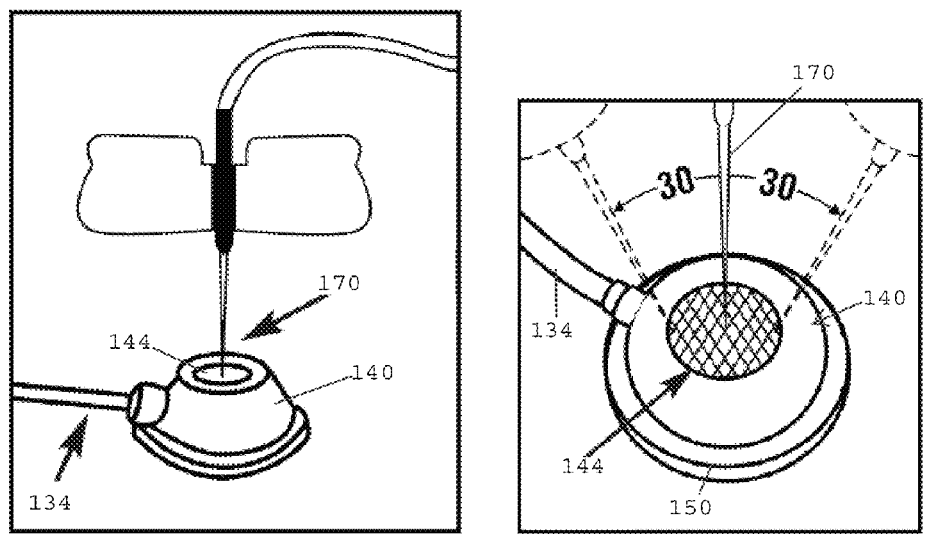
FIG. 5
FIG. 6

BREAST IMPLANTS HAVING DRUG-ELUTING RESERVOIRS AND METHODS THEREFOR

BACKGROUND OF THE INVENTION

1. Field of the Invention

The present invention generally relates to breast implants, and more specifically relates to breast implants having drug-eluting membranes incorporated therein for diffusing therapeutic solutions, such as antibiotic solutions, into surrounding tissue to minimize the chances of infection, rejection, and/or post-implantation complications.

2. Description of the Related Art

Implantable prostheses are commonly used to replace or augment body tissue. In the case of the female breast, it sometimes necessary to remove some or all of the mammary gland and surrounding tissue in order to treat breast cancer. This surgery leaves a void that can be filled with an implantable prosthesis that supports surrounding tissue and maintains the appearance of the body. The restoration of the normal appearance of the body has an extremely beneficial psychological effect on post-operative patients, eliminating much of the shock and depression that often follows extensive surgical procedures. Implantable mammary prostheses are also used for enlargement of the breast, commonly referred to as breast augmentation.

Implantable mammary prostheses, commonly referred to as breast implants, are usually formed of a silicone polymer shell and are filled with saline or silicone gel. Such implants generally have a substantially flat posterior face that is positioned against a patient's chest and a domed anterior face. It is often desirable for a perimeter region of the implant, i.e., the region where the anterior and posterior faces meet, to have a relatively small radius of curvature, particularly at the upper end of the implant. A relatively small radius of curvature in the transition between the anterior face and the posterior face in the upper pole region of the prosthesis is desirable because it permits a relatively smooth transition between the mammary tissue and the implant when the prosthesis is implanted. However, a small radius is sometimes associated with the appearance of creases that extend inward from the perimeter of the prosthesis, which is commonly referred to as "scalloping." Scalloping tends to occur when the prosthesis is filled with fluid and the patient is upright such that the weight of the filling material is pulling downward on the prosthesis. The creases often appear on the anterior face of the prosthesis, which can be aesthetically undesirable as the creases can sometimes be discerned through the overlying skin of the patient.

Breast implants are typically manufactured by dipping an appropriately sized and shaped mandrel in a biocompatible elastomer such as silicone. In one common procedure, the mandrel is dipped into a silicone dispersion and then removed to allow partial cure or solvent evaporation. The dipping and curing process is generally repeated several times. Once the shell has been formed it is removed from the mandrel. The dip-molding process results in the formation of an implant shell that has an opening, e.g., a circular hole (mandrel hole) in one of its faces. The mandrel hole is subsequently covered with a patch that seals the hole, thus forming a complete, fluid impervious shell. The patch is attached to the implant shell using silicone rubber or other similar biocompatible adhesive. The patched shell is sometimes provided with a fill port or valve extending through a face of the prosthesis. The completed shell can either remain unfilled, be pre-filled, or intra-operatively filled through the small fill port or valve with saline, gel, foam, or combinations of these materials. The fill port or valve is sealed or closed, and the implant is sterilized.

After implantation, breast implants are subject to complications from infection. A breast implant infection may manifest itself with clinical symptoms, or there may be no outwardly noticeable symptoms. When a breast implant infection becomes established, a bacterial biofilm typically forms around or in areas of the implant surface. The biofilm, a proteoglycan polysaccharide produced by the bacteria, protects the bacteria from being affected by even high concentrations of antibiotics. Thus, once the infection takes hold, conventional concentrations of systemic antibiotics cannot eliminate the infection but can only keep it from spreading further. Thus, a chronic subclinical inflammatory situation develops, which may lead to eventual implant rejection.

Symptomatic infections usually result in the removal of the implant. Non-symptomatic infections (i.e. sub-clinical) may lead to chronic inflammatory responses that can be a major cause of collagen capsular contracture. Capsular contracture is one of the major drawbacks of breast augmentation and reconstruction using silicone implants.

In view of the foregoing, there is a need for breast implants, breast implant systems and surgical techniques that can reduce or eliminate infection and the resulting capsular contracture. Such an implant would represent a major improvement in breast implant performance and patient satisfaction.

SUMMARY OF THE INVENTION

In one embodiment, a breast implant preferably includes an implant shell having an outer surface and defining a first reservoir, and a porous membrane overlying the outer surface of the implant shell and defining a second reservoir located between the outer surface of the implant shell and the porous membrane. The implant desirably includes a filling tube having a first conduit in communication with the first reservoir of the implant shell and a second conduit in communication with the second reservoir located between the implant shell and the porous membrane. The implant may include an injection dome coupled with the filling tube and having a first fluid chamber in fluid communication with the first conduit of the filling tube and a second chamber in fluid communication with the second conduit of the filling tube.

In one embodiment, the injection dome preferably includes an upper end including an injection cover and a lower end including a support base. The first chamber is preferably located adjacent the injection cover, and the second chamber is preferably located adjacent the support base. The injection dome desirably includes a diaphragm extending between the first and second chambers for separating the first and second chambers from one another.

In one embodiment, the injection cover is preferably pierceable by an injection needle for introducing a first solution into the first chamber of the injection dome for supplying the first solution to the first reservoir of the implant. The diaphragm of the injection dome is desirably pierceable by an injection needle for introducing a second solution into the second chamber of the injection dome for supplying the second solution to the second reservoir of the implant. In one embodiment, the injection cover and the diaphragm are preferably made of self-sealing materials adapted to seal holes formed by injection needles when the injection needles are withdrawn from the injection cover and/or the diaphragm. In one embodiment, a bottom surface or support base of the injection dome is made of metal for preventing a needle from passing through the base.

In one embodiment, the first solution introducible into the first reservoir of the implant is preferably a saline solution. The second solution introducible into the second reservoir of the implant is preferably a drug solution including, but not limited to, antibiotics, anti-fungals, anti-bacterials, hormones, steroids, and/or combinations thereof.

In one embodiment, the implant shell is adapted to expand upon introducing a saline solution into the first reservoir. The implant shell may be filled this saline solution.

In one embodiment, the implant shell includes a silicone shell, and the porous membrane includes a porous silicone patch that covers at least a portion of the outer surface of the implant shell. In one embodiment, the porous membrane is desirably attached to the outer surface of the implant shell. In one embodiment, the porous membrane completely surrounds the outer surface of the implant shell.

In one embodiment, the filling tube preferably has a distal end and a proximal end, whereby the distal end of the filling tube is coupled with the implant shell and the proximal end of the implant shell is coupled with the injection dome. The filling tube may be a dual lumen filling tube. The distal end of the filling tube may be releasably coupled with the implant shell.

In one embodiment, a breast implant preferably includes an implant shell including a first fluid reservoir, and a porous membrane covering an outer surface of the implant shell for defining a second fluid reservoir that is distinct from the first fluid reservoir. The implant preferably includes a filling tube having a first conduit in communication with the first fluid reservoir chamber and a second conduit in communication with the second fluid reservoir. An injection dome is desirably coupled with the filling tube and includes a first chamber in communication with the first conduit for supplying a first solution to the first fluid reservoir of the implant, a second chamber in communication with the second conduit for supplying a second solution to the second fluid reservoir, and a diaphragm separating the first and second chambers from one another.

In one embodiment, a breast implant preferably includes an implant shell having an outer surface, a porous membrane overlying the outer surface of the implant shell and defining an outer reservoir located between the outer surface of the implant shell and the porous membrane. The implant shell may be pre-filled with a gel or a saline solution. In one embodiment, the implant shell is not adapted for expansion after implantation. A filling tube is preferably in communication with the outer reservoir of the implant for supplying a drug solution to the outer reservoir. The porous membrane is preferably adapted to diffuse any drug solution disposed therein into tissue surrounding the implant shell. In one embodiment, the implant shell preferably defines an internal reservoir located within the implant shell. In one embodiment, the filling tube desirably includes a first conduit in communication with the internal reservoir and a second conduit adapted to supply the drug solution to the outer reservoir.

These and other preferred embodiments of the present invention will be described in more detail below.

BRIEF DESCRIPTION OF THE DRAWING

FIGS. 1A-1C show a breast implant including an implant shell and a drug-eluting reservoir, in accordance with one embodiment of the present invention.

FIG. 2A shows a cross-sectional view of an expandable breast implant having a drug eluting reservoir, a filling tube and an injection dome, in accordance with one embodiment of the present invention.

FIGS. 3A-1 through 3B-1 show a cross-sectional view of the injection dome during the steps shown in FIGS. 3A and 3B.

FIG. 4 shows a syringe and a check valve adapted to be assembled with a proximal end of a filling tube of a breast implant, in accordance with one embodiment of the present invention.

FIGS. 5 and 6 show a method of using an injection needle for injecting a solution into an injection dome, in accordance with one embodiment of the present invention.

FIGS. 11A-1 through 11C-1 show a cross-sectional view of an injection dome during the steps shown in FIGS. 11A-11C.

FIGS. 12A-1 through 12C-1 show a cross-sectional view of an injection dome during the steps shown in FIGS. 12A-12C.

DETAILED DESCRIPTION

Figure 1B:
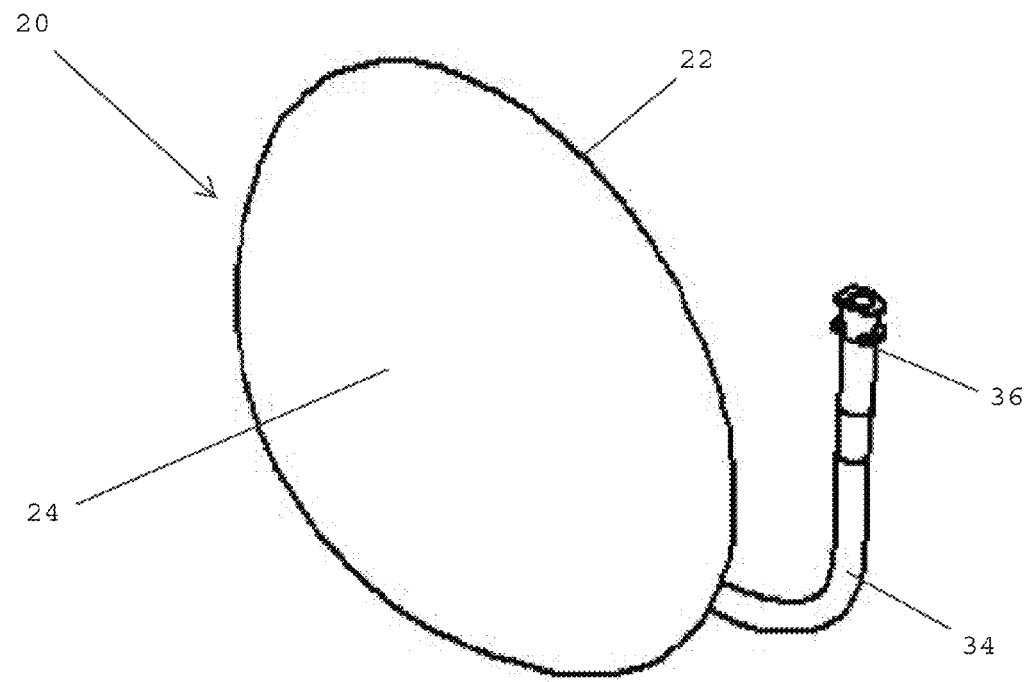
Figure 1C:
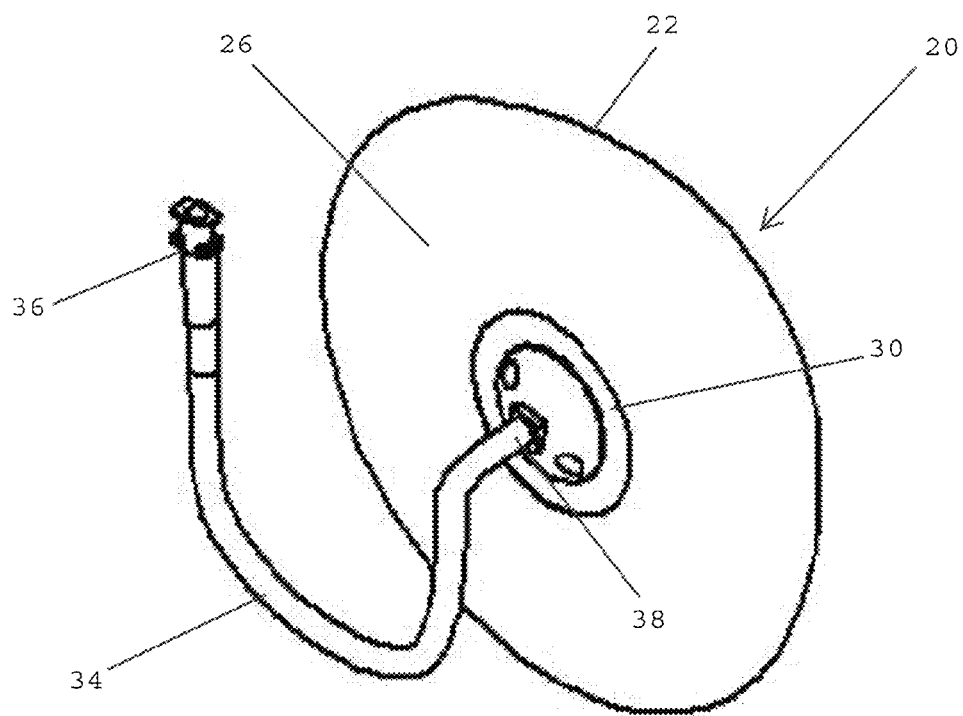

Referring to FIGS. 1A-1C, in one embodiment, a breast implant 20 preferably includes an implant shell 22, such as a silicone shell, that defines an outer surface of the implant. The implant shell is preferably adapted for being implanted within a pocket formed in breast tissue. The implant shell 22 described has an anterior face 24 and a posterior face 26. In one embodiment, the implant shell 22 is desirably formed using a mandrel. As such, the implant shell 22 may include a mandrel hole (not shown) that extends through the outer wall of the shell, and which may be used for removing the implant shell 22 from the mandrel after the shell has been formed thereon. In one embodiment, the mandrel hole preferably extends through a posterior face 26 of the implant shell 22. In other embodiments, however, the mandrel hole may be formed on an anterior face of the implant shell. In one embodiment, the mandrel hole may be used for introducing a solution, such as saline solution, a gel, or a saline-gel combination inside the implant shell 22. In one embodiment, the mandrel hole is always patched before the saline, gel, or saline-gel combination is added into the shell.

In one embodiment, the gel is preferably introduced into the implant shell as a reactive fluid that is cured using heat. The fluid reactive gel is preferably added through a small hole made by a syringe needle and subsequently sealed by silicone adhesive. For a saline implant, the saline is preferably added after implantation through a fill-tube. The fill-tube may be removed from a fill-valve for sealing the implant opening.

In one embodiment, the breast implant 20 preferably includes a porous membrane 28, such as a silicone patch, that is adapted to cover the mandrel hole patch on the posterior face 26 of the implant shell 22. The porous membrane 28 is desirably formed using various techniques well known to those skilled in the art, such as those disclosed in U.S. Pat. No. 7,410,480, the disclosure of which is hereby incorporated by reference herein. In one embodiment, the porous membrane 28 is preferably adhered to an outer surface (e.g. the posterior face) of the implant shell 22 so that it may not be easily removed. The porous membrane and the outer surface of the implant shell preferably define an enclosed reservoir 30 therein that is adapted to receive a solution such as a pharmaceutical solution. The porous membrane 28 preferably allows diffusion of solutions, such as drug solutions, at a predetermined rate into the tissue surrounding the membrane and the implant shell. As will be described in more detail below, the porous membrane 28 may incorporate, or may be positioned adjacent, one or more valves for enabling solutions, such as silicone gels, saline solutions, and pharmaceutical solutions, to be introduced through the porous membrane 28 and into the reservoir 30.

In one embodiment, the breast implant 20 preferably includes a filling tube 34 used for introducing solutions into the reservoir 30 defined by the porous membrane 28. In one embodiment, the filling tube 34 desirably includes a proximal end 36 and a distal end 38 that is remote from the proximal end. The proximal end 36 of the filling tube 34 is preferably adapted to be coupled with a syringe or an injection dome. The injection dome coupled with the proximal end of the filling tube may be a single chamber injection dome or a double chamber injection dome. In one embodiment, the proximal end 36 of the filling tube 34 may be directly coupled with a syringe. The distal end 38 of the filling tube 34 is preferably adapted to be selectively decoupled from the porous membrane 28 after desired quantities of solution have been introduced into the enclosed reservoir 30.

In one embodiment, after the implant shell 22 is implanted inside a tissue pocket, the distal end 38 of the filling tube 34 remains attached to the porous membrane 28 and the proximal end 36 of the filling tube remains accessible to medical personnel for introducing solutions through the filling tube and into the reservoir 30 defined by the porous membrane 28. The distal end 38 of the filling tube 34 is preferably releasably attached to the porous membrane 28. In one embodiment, an initial dose of solution is introduced into the reservoir 30 for being diffused through the porous membrane and into the tissue surrounding the implant. The initial dose may be introduced by a syringe needle. After a period of time, a second dose of solution may be introduced into the reservoir 30 for re-filling the reservoir with the solution. The second and any subsequent doses may be introduced using a syringe needle or an injection dome. The filling procedure may be repeated as many times as necessary in order to prevent infection and insure acceptance of the implant by the body. Once medical personnel are satisfied that no additional doses of solution are required to be introduced into the reservoir, the distal end 38 of the filling tube 34 may be decoupled from the porous membrane 28. As the decoupling occurs, one or more valves, preferably within or adjacent the porous membrane automatically close to prevent leaking of the dose of the solution loaded into the reservoir 30.

Referring to FIG. 2A, in one embodiment, a breast implant 120 preferably includes an implant shell 122, such as a silicone shell, defining a first reservoir 124 adapted to receive a first solution such as a silicone gel, a saline solution, or a combination gel-saline solution. The implant shell 122 is preferably impermeable so that the first solution introduced therein may not pass through the shell. In one embodiment, the first solution may be introduced into the first reservoir 124 for increasing the size of the implant 120, such as during breast augmentation or reconstruction procedures. The breast implant 120 also preferably includes a porous membrane 128 that desirably surrounds at least a portion of the outer surface of the implant shell 122. The porous membrane 128 preferably defines a second reservoir 130 that at least partially surrounds the implant shell 122 and at least a portion of the first internal chamber 124. In one embodiment, the second reservoir 130 is preferably adapted to receive a second solution, such as a drug solution, that is different than the first solution introduced into the first internal chamber 124. In one embodiment, the porous membrane 128 is preferably adapted to enable the second solution introduced into the second reservoir to, over time, diffuse through the porous membrane for bathing the breast tissue surrounding the implant 120. The size, shape, pattern and number of pores provided in the porous membrane 128 may be modified to maximize therapeutic benefit, and may change depending upon the particular drug solution used.

In one embodiment, the breast implant 120 also preferably includes a patch 135, such as a silicone patch, adhered to a posterior face 132 of the implant 120. The patch 135 may cover a mandrel hole extending through the implant shell 122 and/or the porous membrane 128, and preferably includes structure for enabling a distal end 138 of a filling tube 134 to be releasably coupled with the implant 120 for introducing solutions into the respective first and second reservoirs 124, 130 of the implant.

In one embodiment, the filling tube 134 is preferably used for introducing solutions through the patch 135 and into the respective first and second reservoir 124, 130 of the implant. In one embodiment, the filling tube 134 desirably includes a proximal end 136 and a distal end 138. The proximal end 136 of the filling tube 134 is preferably adapted to be coupled with a syringe or an injection dome 140. The distal end 138 of the filling tube 134 is preferably adapted to be selectively decoupled from the patch 135 after desired quantities of the two solutions have been introduced into the implant 120.

In one embodiment, the filling tube 134 is preferably a dual lumen filling tube including a first conduit 142 extending between the proximal and distal ends 136, 138 thereof for introducing a first solution into the first reservoir 124 of the implant 120. The dual lumen filling tube 134 also preferably includes a second conduit 144 extending between the proximal and distal ends 136, 138 thereof for introducing a second solution into the second reservoir 130 of the implant 120.

Figure 2B:
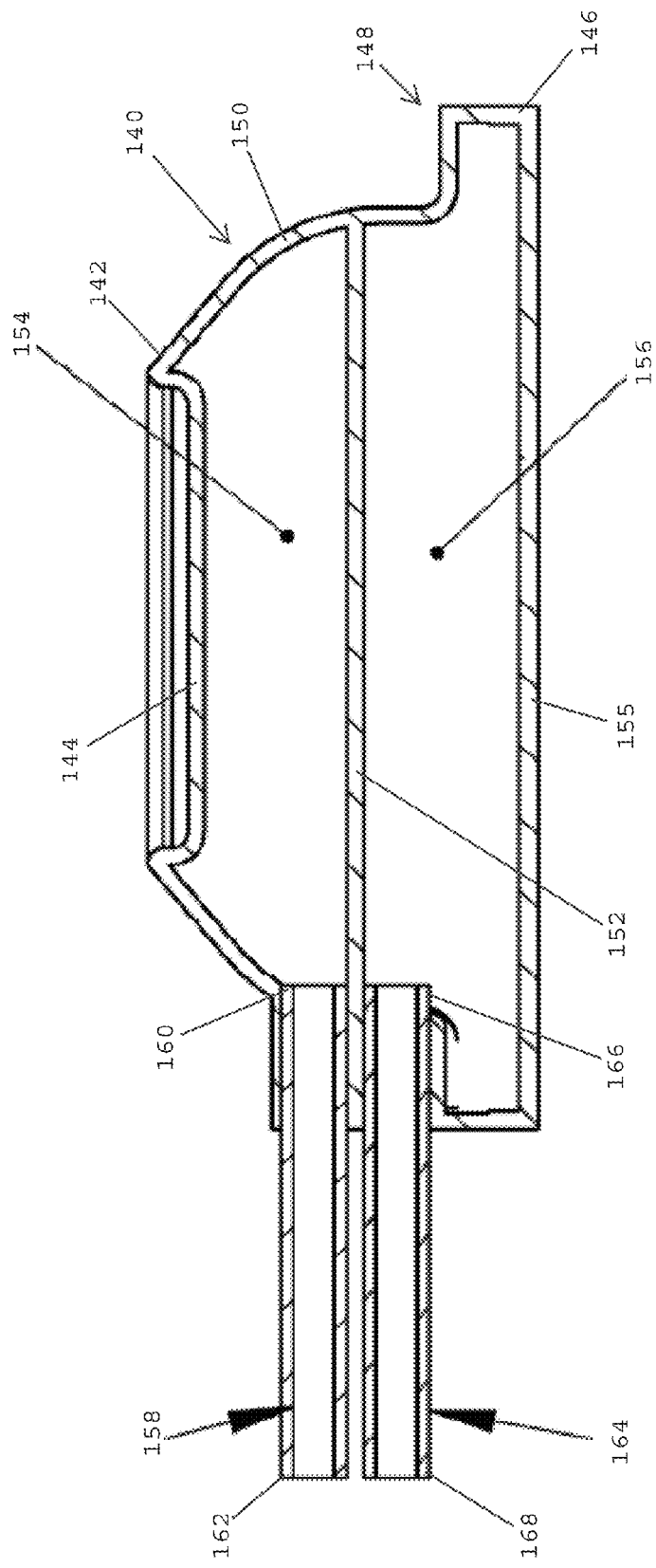
FIG. 2B shows a cross-sectional view of the injection dome shown in FIG. 2A.

Referring to FIG. 2B, in one embodiment, the injection dome 140 is preferably a dual chamber injection dome adapted to be coupled with the proximal end 136 of the dual lumen filling tube 134 for introducing two different solutions into the respective first and second reservoirs 124, 130 of the breast implant 120. The injection dome may comprise silicone elastomer. In one embodiment, the dual chamber injection dome 140 preferably includes an upper end 142 having a centrally located injection cover 144, a lower end 146 defining a base 148, and a sidewall 150 extending between the upper and lower ends 142, 146. In one embodiment, the sidewall 150 of the injection dome 140 preferably has a dome-like shape. In one embodiment, the injection cover 144 preferably includes a self-sealing material such as a silicone gel or compression ring that forms a water-tight seal after an injection needle has been removed therefrom.

In one embodiment, the dual chamber injection dome 140 preferably includes a diaphragm 152 that divides the injection dome into a first chamber 154 adapted to receive a first solution, such as a saline solution, and a second chamber 156 adapted to receive a second solution, such as a drug solution. The diaphragm 152 preferably includes a self-sealing material such as a silicone gel or compression ring for maintaining a water-tight seal between the first and second chambers 154, 156. Thus, an injection needle may be inserted through the injection cover 144 and the diaphragm 152 for introducing a solution into the second chamber 156. When the needle is withdrawn from the diaphragm 152, any opening formed by the injection needle in the diaphragm will close as the needle is withdrawn. In one embodiment, medical personnel preferably use tactile feedback for determining when the injection needle has pierced through the diaphragm 152 and advanced into the second chamber 156. In one embodiment, the bottom face 155 of the dual chamber injection dome 140 is preferably made of a strong material, such as stainless steel, that is difficult to pierce using an injection needle for minimizing the likelihood of an injection needle advancing through the bottom of the injection dome 140.

In one embodiment, the dual chamber injection dome 140 preferably includes a first coupler 158 for providing a fluid path between the first chamber 154 of the injection dome 140 and the first conduit 142 extending through the dual lumen filling tube 134 (FIG. 2A). The first coupler 158 preferably includes a proximal end 160 having an opening in communication with the first chamber 154 and a distal end 162 having an opening adapted to transfer the first solution into the first conduit 142 of the dual lumen filling tube 134. The injection dome 140 also preferably includes a second coupler 164 for providing a fluid path between the second chamber 156 of the injection dome 140 and the second conduit 144 extending through the dual lumen filling tube 134. The second coupler 164 preferably includes a proximal end 166 having an opening in communication with the second chamber 156 and a distal end 168 having an opening adapted to transfer the second solution into the second conduit 144 of the dual lumen filling tube 134.

Referring to FIG. 2A, in one embodiment, the distal end 138 of the filling tube 134 is releasably coupled with the implant 120 and may be selectively decoupled from the implant by tugging on a section of the filling tube 134. As the distal end of the filling tube is decoupled, valves (not shown) in communication with the first and second chambers 124, 130 will desirable automatically close to seal any openings in the implant 120 so as to prevent fluid leaks.

Referring to FIGS. 2A and 2B, in one embodiment, the injection dome 140 is preferably coupled with the proximal end 136 of the dual lumen filling tube 134. As noted above, the injection dome 140 desirably includes a first chamber 154 adapted to receive a first solution, such as a saline solution, and a second chamber 156 adapted to receive a second solution, such as a drug solution. The first and second chambers 154, 156 are preferably separated from one another by the diaphragm 152. The first and second solutions may be introduced into the respective first and second chambers 154, 156 by passing a distal end of an injection needle 170 through the injection cover 144 provided at the upper end 142 of the injection dome 140. The injection dome 140 preferably includes the first coupler 158 that is adapted to pass the first solution from the first chamber 154 into the first conduit 142 of the filling tube 134 for selectively filling the first reservoir 124. The injection dome 140 preferably includes the second coupler 164 adapted to pass the second solution from the second chamber 156 into the second conduit 144 of the filling tube 134 for selectively filling the second reservoir 130.

Figure 3A:
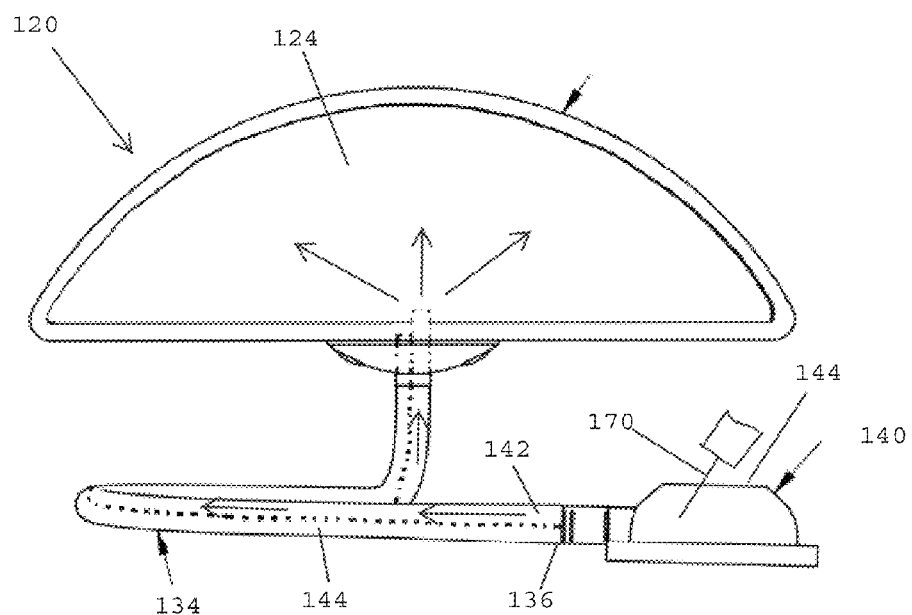
FIGS. 3A and 3B show a method of introducing solutions into the breast implant of FIGS. 2A and 2B, in accordance with one embodiment of the present invention.
Figures 1, 3A:
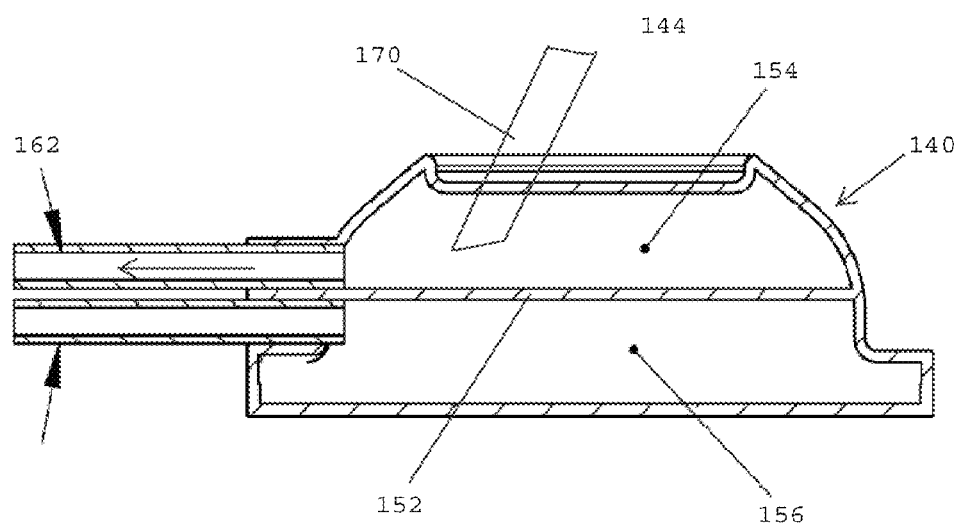

Referring to FIGS. 3A and 3A-1, in one embodiment, an injection needle 170 is preferably passed through the injection cover 144 of the injection dome 140 for introducing the first solution into the first chamber 154 of the injection dome 140. As the solution is dispensed into the first chamber 154, the solution passes through the first coupler 162 of the injection dome and into the first conduit 142 of the filling tube 130. The solution travels downstream in the direction indicated by the arrows until it is dispensed into the first internal reservoir 124 of the expandable implant 120. As the first solution fills the first reservoir 124, the size of the expandable implant 120 may increase. In one embodiment, a surgeon may introduce additional doses of the first solution into the first reservoir 124, if necessary. In one embodiment, medical personnel may reverse the procedure for removing some of the first solution from the first reservoir 124.

Figure 3B:
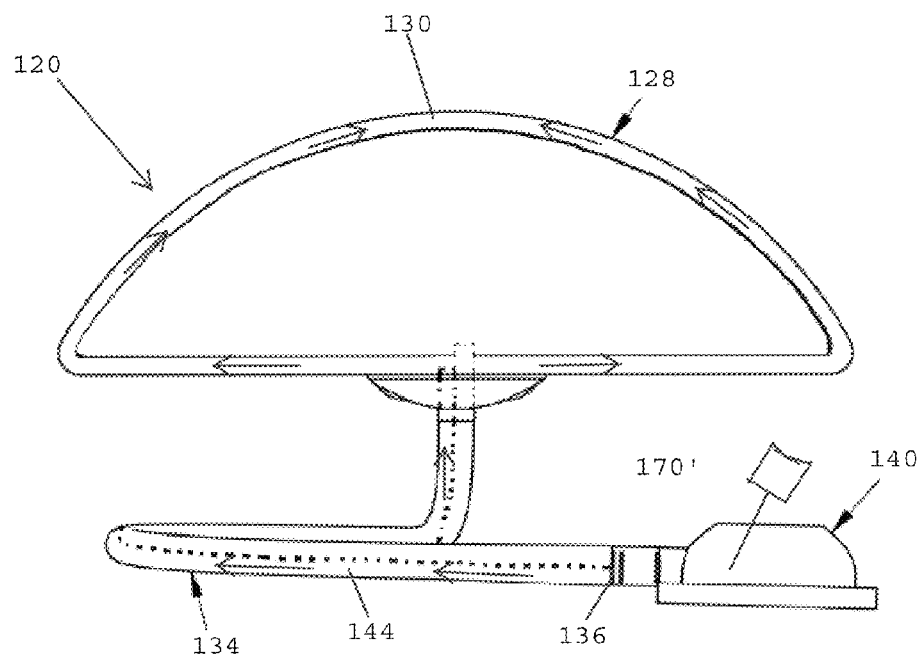
Figures 1, 3B:
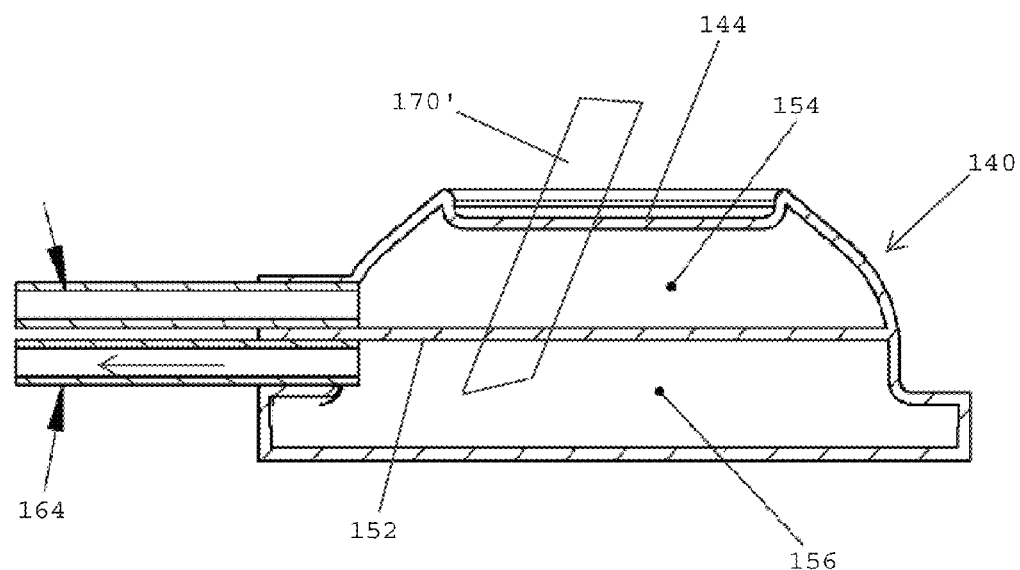

Referring to FIGS. 3B and 3B-1, in one embodiment, it may be desirable to introduce a second solution, such as an antibiotic or drug solution, into the second reservoir 130 of the implant 120. In one embodiment, this may be accomplished by advancing a second injection needle 170' through the injection cover 144 and the diaphragm 152 until a distal end of the second needle is disposed within the second chamber 156 of the injection dome 140. The second solution preferably passes through the second coupler 164 of the injection dome 140 and into the second conduit 144 of the filling tube 134. The second solution desirably flows in the direction of the arrows shown in FIGS. 3B and 3B-1 for flowing into the second reservoir 130 defined by the porous membrane 128. In one embodiment, the porous membrane 128 preferably includes a plurality of openings that enable the second solution to diffuse through the membrane 128 for bathing the breast tissue surrounding the implant 120 with the second solution.

Referring to FIG. 4, in one embodiment, a syringe 180 may be used for filling an implant with a solution such as a saline or drug solution. In one embodiment, a filling tube 134 has a proximal end 136 that is coupled with the syringe 180 using a luer adapter 182 and a two-way check valve 184. After the syringe 180 is coupled with the proximal end of the filling tube 134, a plunger 186 on the syringe 180 may be depressed for injecting the solution through the filling tube 134 and into a breast implant. If necessary, the plunger 186 may be retracted relative to a distal end of the syringe 180 for removing fluid or solution from the implant. The arrangement shown in FIG. 4 is preferably used during a surgical procedure when a breast implant is initially disposed within a tissue pocket and filled with a solution for expanding the implant or bathing the tissue surrounding the implant with a solution such as a drug solution.

Referring to FIG. 5, in one embodiment, the injection dome 140 preferably includes an area that adapted to receive an injection needle 170. In one embodiment, the area adapted to receive an injection needle is defined by an injection cover 144. In one embodiment, a distal end of the injection needle 170 may be passed through the injection cover 144 for introducing one or more solutions into the injection dome 140. As the solution is introduced into the injection dome 140, the fluid preferably passes downstream through a filling tube 134 and into a reservoir located within an implant.

Referring to FIG. 6, in one embodiment, the distal end of the injection needle 170 is preferably passed through the injection cover 144 provided at the upper end of the injection dome 140. As shown in FIG. 6, in one embodiment, the injection needle 170 preferably forms an angle of no greater than 30 degrees with the top surface of the injection cover 144 so that the distal end of the needle 170 does not pierce a sidewall 150 of the injection dome. When the solution is dispensed inside the injection dome 140, the solution preferably advances downstream through the filling tube 134 for expanding the implant and/or providing a drug solution to the implant.

Figure 7A:
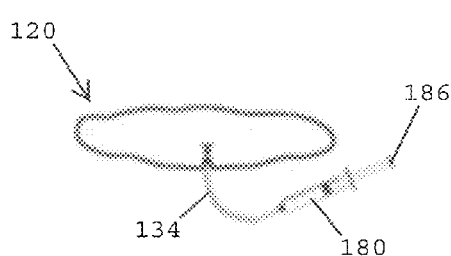
FIG. 7A-7E show a method of introducing solutions into a breast implant using a filling tube and an injection dome, in accordance with one embodiment of the present invention.

FIGS. 7A-7E show one preferred method for providing first and second solutions to a breast implant 120. Referring to FIG. 7A, in one embodiment, an expandable implant 120 is implantable within a tissue pocket of a patient. In the stage shown in FIG. 7A, the implant 120 is at least partially collapsed. In order to initially fill the implant 120 with one or more solutions, the implant 120 may be coupled with a dual lumen filling tube 134, which, in turn, is coupled with a syringe 180 having a plunger 186. The plunger 186 is preferably depressed for injecting a first solution into a first internal reservoir 124 of the implant for expanding the size of the implant to the configuration shown in FIG. 7B.

Figure 7B:
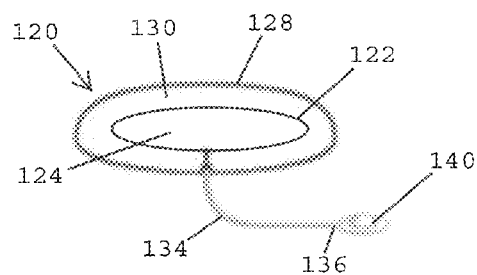

As shown in FIG. 7B, in one embodiment, the expandable breast implant 120 preferably includes a silicone shell 122 that defines a first internal reservoir 124 and a porous membrane 128 that surrounds the silicone shell 122 for defining a second reservoir 130. In one embodiment, after the initial surgical procedure, the proximal end 136 of the filling tube 134 is preferably coupled with a dual chamber injection dome 140 as shown and described above. The dual chamber injection dome 140 desirably enables two different solutions to be introduced into the expandable implant 120.

Figure 7C:
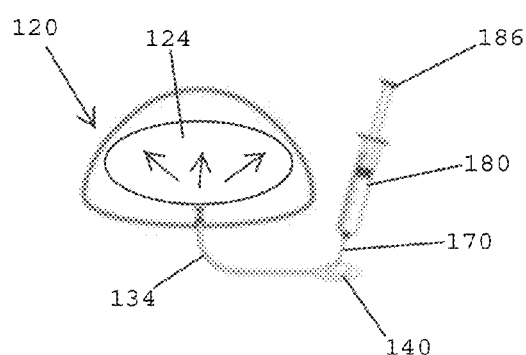

Referring to FIG. 7C, in one embodiment, it may be desirable to add more solution, such as a saline solution, to the first reservoir 124 of the implant so as to increase the size of the implant 120. In order to accomplish this task, a first syringe 180 may be filled with a first solution, such as a saline solution. An injection needle 170 at the distal end of the syringe 180 may be inserted into the first chamber of the injection dome 140. The plunger 186 of the syringe 180 is preferably depressed for dispensing the first solution into the injection dome 140, through the first conduit of the filling tube 134, and into the first reservoir 124 of the expandable implant 120 for increasing the size of the first reservoir 124. As the size of the first reservoir 124 expands, the implant 120 also preferably increases in size.

Figure 7D:
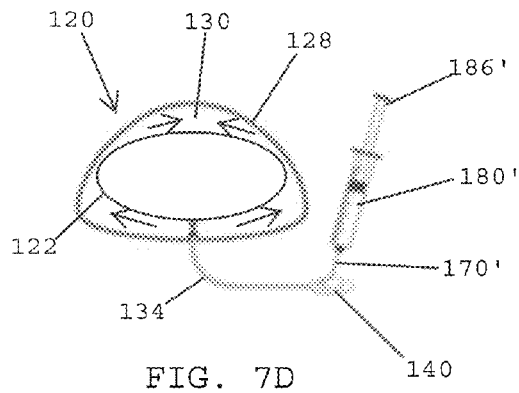

Referring to FIG. 7D, in one embodiment, it may be desirable to introduce a second solution, such as a drug solution, into the second reservoir 130 that surrounds the implant shell 122. In one embodiment, a second syringe 180' is desirably provided that contains a second solution. The injection needle 170' of the second syringe 180' is desirable introduced into the injection dome 140 so that the distal end of the injection needle 170' advances through the diaphragm (FIG. 3B-1) dividing the two chambers of the injection dome and into the second chamber (FIG. 3B-1) of the injection dome 140. The plunger 186' of the syringe 180' is preferably depressed for dispensing the second solution into the second chamber of the injection dome 140, through the second conduit of the filling tube 134 and into the second reservoir 130 of the expandable implant 120. The second solution preferably fills the second reservoir 128 for being diffused over time through the porous membrane 128 for exposing and/or bathing the tissue surrounding the implant with the second solution.

Figure 7E:
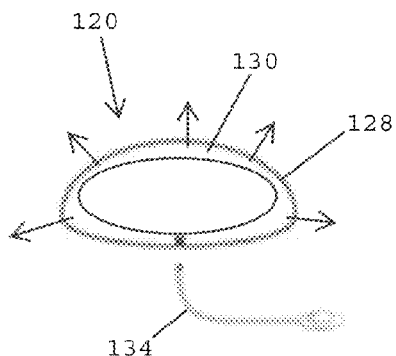

Referring to FIG. 7E, in one embodiment, after the second solution has been introduced into the drug eluting reservoir 130, the filling tube 134 may be de-coupled from the expandable implant 120. In one embodiment, the filling tube 134 may be removed from its coupling with the implant 120 by slightly tugging on the filling tube. In one embodiment, the implant 120 desirably includes one or more valves that automatically close when the filling tube 134 is detached from the implant 120. After the filling tube 134 has been detached, the implant 120 preferably remains in place in the tissue pocket. The drug solution disposed within the second reservoir 130 preferably diffuses outwardly through the porous membrane 128 to provide a continuous drug solution to the tissue surrounding the implant 120.

Figure 8A:
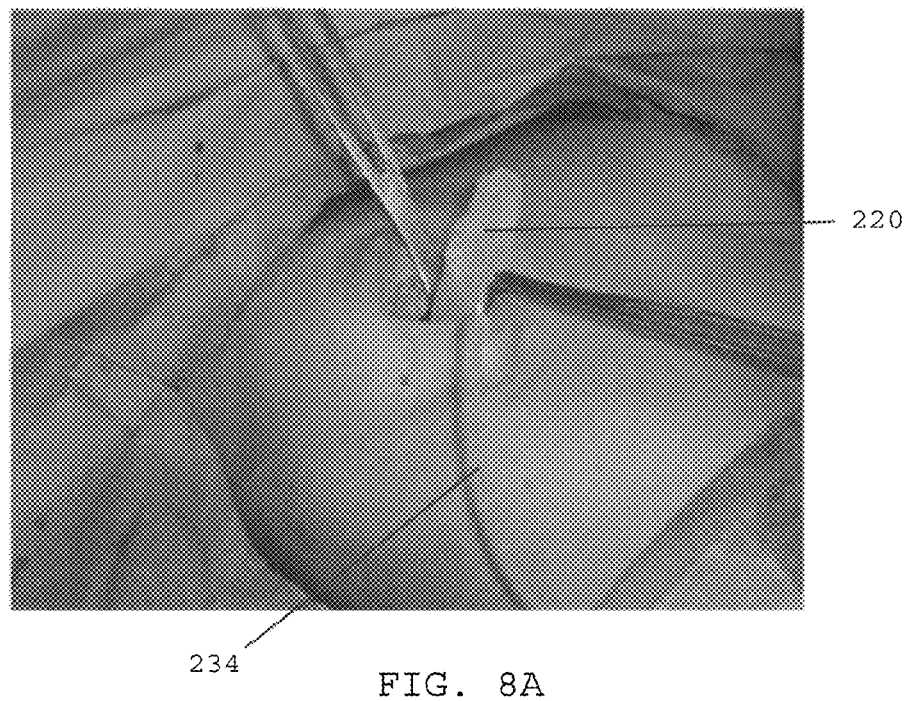
FIGS. 8A-8F show a method of implanting and introducing solutions into an expandable breast implant, in accordance with one embodiment of the present invention.

Referring to FIG. 8A, in one embodiment, an expandable breast implant 220 is passed through a surgical opening so that it may be placed within a pocket formed in breast tissue. As will be described in more detail below, the implant 220 preferably includes a first internal chamber or reservoir adapted to receive a first solution, and a second outer chamber or reservoir adapted to receive a second solution that diffuses into the tissue surrounding the implant. The implant 220 is preferably coupled with a dual lumen filling tube 234 that is used for selectively injecting the first and second solutions into the respective reservoirs of the implant 220.

Figure 8B:
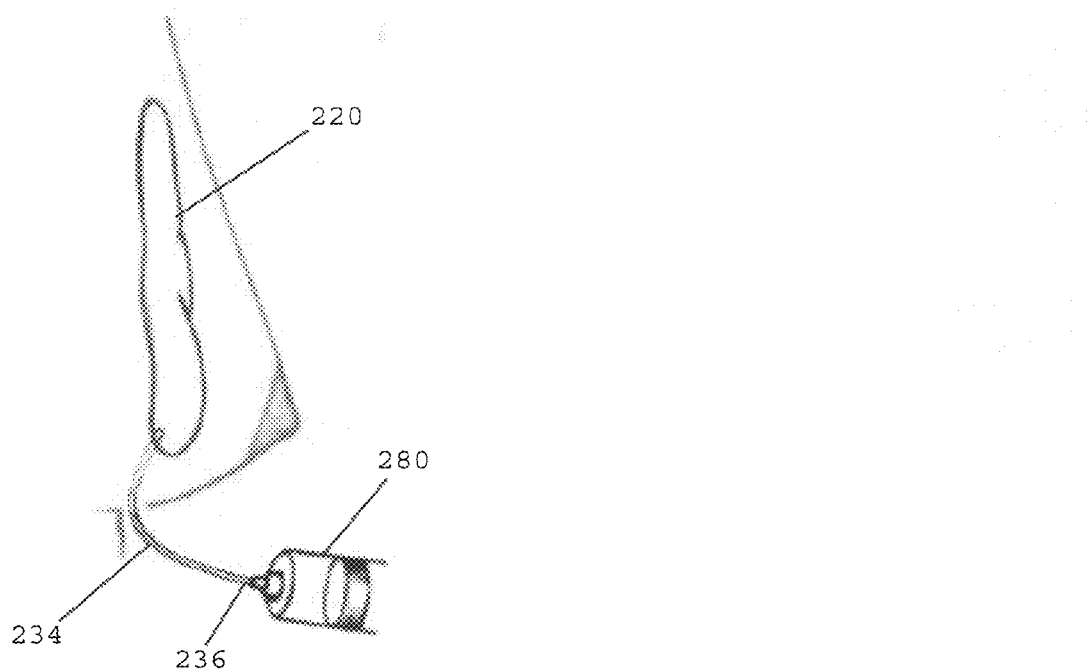

Referring to FIG. 8B, in one embodiment, the implant 220 is inserted into the pocket formed in the breast tissue in an at least partially collapsed state. The dual lumen filling tube 234 preferably extends outside the patient's body so that a proximal end 236 of the filling tube 234 may be coupled with a fluid filled syringe 280. A plunger (not shown) on the syringe 280 may be depressed for introducing a first solution into the first reservoir of the implant 220. A second solution, such as a drug solution, may be introduced into the second reservoir of the implant using similar techniques. After the surgeon is satisfied that the implant 220 has been expanded to a sufficient size, or after the surgeon is satisfied that sufficient drug solution has been introduced, the syringe 280 is preferably de-coupled from the proximal end 236 of the filling tube 234 and replaced with an injection dome 240 (FIG. 8C).

Figure 8C:
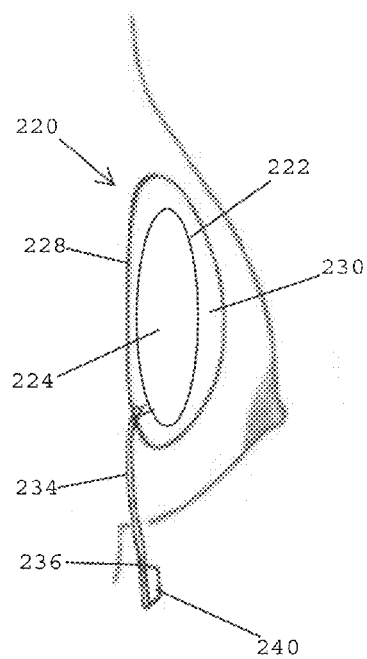

FIG. 8C shows the implant 220 after the initial surgical procedure described above is complete. The expandable implant 220 is desirably coupled to a filling tube 234 that extends outside of the patient's body. A proximal end 236 of the filling tube 234 is preferably coupled with an injection dome 240. The expandable implant 220 desirably includes an implant shell 222, such as a silicone shell, that surrounds a first reservoir 224 and a porous membrane 228 that surrounds a second reservoir 230. The actual spacing between the porous membrane 228 and the implant shell 222 may be less than what is shown in FIG. 8C, which is not to scale and which has been prepared to more clearly show the various parts of one preferred implant.

Figure 8D:
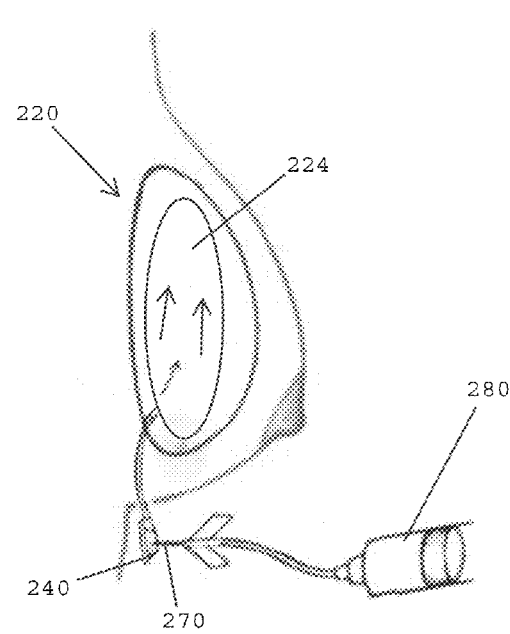

Referring to FIG. 8D, in one embodiment, it may be desirable to expand the size of the implant 220 after the initial surgery. In order to introduce additional solution into the first reservoir 224 of the implant 220, an injection needle 270 is preferably advanced into the injection dome 240. A plunger on the syringe 280 is preferably depressed for injecting the solution into the injection dome 240, which, in turn, passes the additional solution into the first reservoir 224 for increasing the size of the implant 220.

Figure 8E:
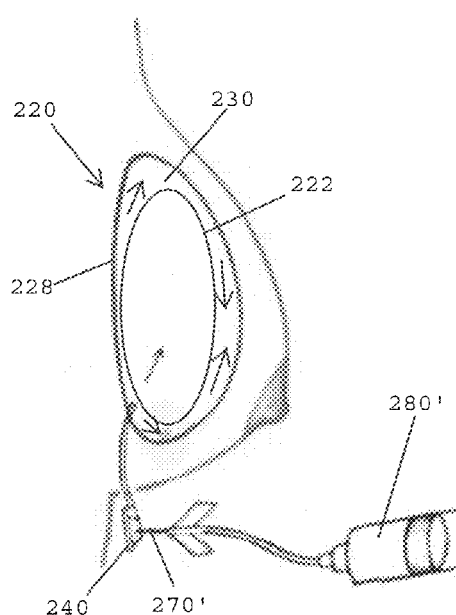

Referring to FIG. 8E, in one embodiment, it may be desirable to introduce a second solution into the outer reservoir 230 that at least partially surrounds the silicone shell 222. In one embodiment, a second injection needle 270' is inserted into the second chamber of the injection dome 240. A plunger on a second syringe 280' is depressed for introducing the second solution into the injection dome 244, which, in turn, passes the second solution into the second outer reservoir 230 surrounding the silicone shell 222. The membrane 228 defining the second reservoir 230 is desirably porous so that the second solution within the second reservoir is free to pass therethrough and into the tissue surrounding the implant 220.

Figure 8F:
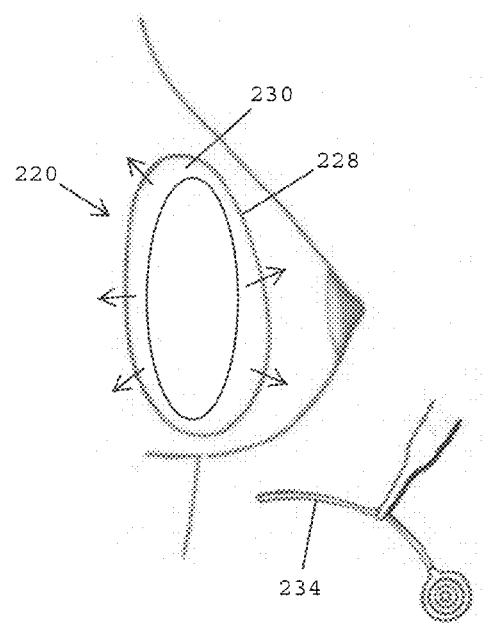

Referring to FIG. 8F, in one embodiment, after the surgeon pr medical personnel are satisfied that no further solutions need to be introduced into the implant 220, the surgeon or medical personnel may de-couple the filling tube 234 from the expandable implant 220. In one embodiment, a forceps-like tool may be utilized for tugging on a section of the filling tube 234 that is accessible outside the patient's body. As soon as the filling tube 234 is de-coupled from the implant, the one or more valves interconnecting the filling tube with the implant automatically close for sealing the implant 220 and preventing leaks. After the filling tube 234 has been removed, the second solution present in the outer reservoir 230 preferably continues to diffuse through the porous membrane 228 for bathing the breast tissue surrounding the implant with the second solution.

Figure 9:
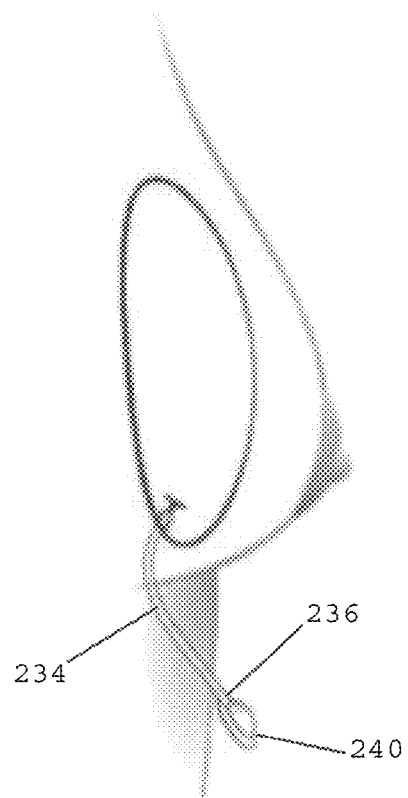
FIG. 9 shows a breast implant coupled with an injection dome located outside a patient's body, in accordance with one embodiment of the present invention.
Figure 10:
FIG. 10 shows a breast implant coupled with an injection dome implanted under a patient's skin, in accordance with one embodiment of the present invention.

Referring to FIG. 9, in one embodiment, the proximal end 236 of the filling tube 234 preferably extends outside the patient's body so that the injection dome 240 may be accessible outside the body. Referring to FIG. 10, in one embodiment, the entire length of the filling tube 334 and the injection dome 340 are positioned below a patient's skin surface. Additional fluid may be introduced into the injection dome 340 by advancing an injection needle through the patient's skin for engaging the injection dome 340.

Figure 11A:
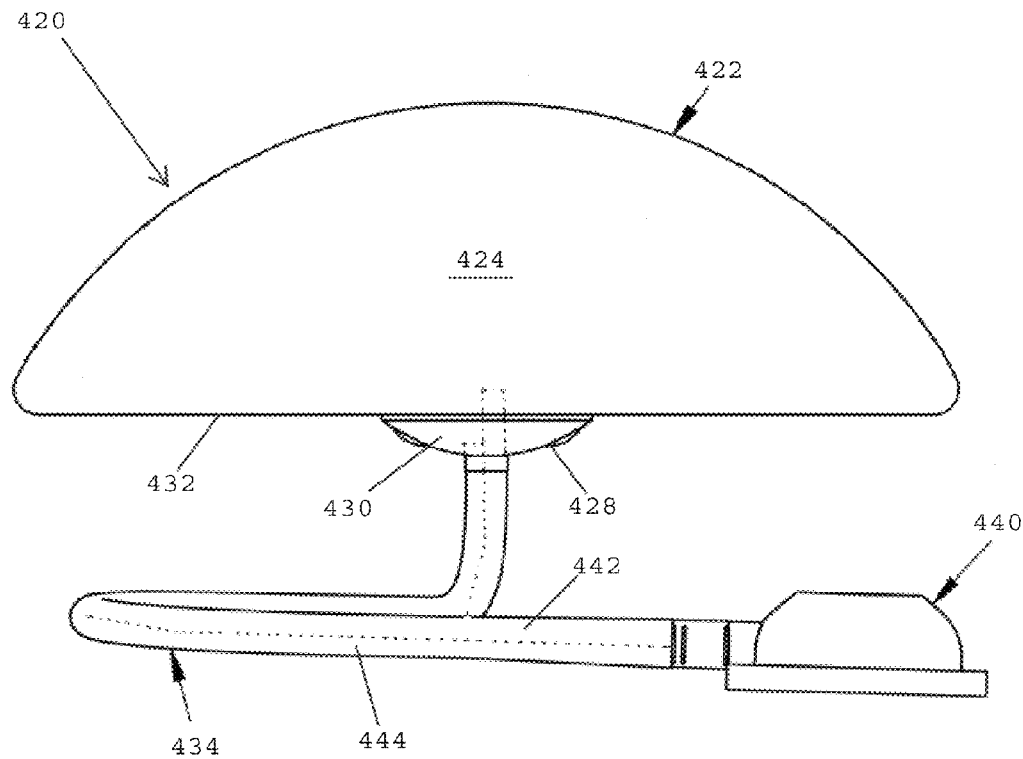
FIGS. 11A-11C show a method of introducing solutions into an expandable breast implant, in accordance with one embodiment of the present invention.
Figures 1, 11A:
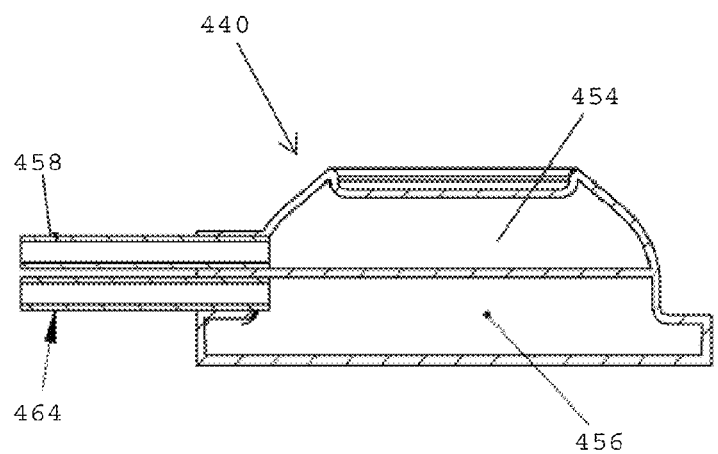

Referring to FIG. 11A, in one embodiment, an expandable breast implant 420 includes an implant shell 422 defining an outer surface of the implant. A posterior surface 432 of the implant is preferably covered by a patch 428, such as a silicone patch, that defines an enclosed space 430. The patch 428 is desirably a porous membrane so that a solution introduced into the enclosed space 430 is able to diffuse through the patch and into the tissue surrounding the implant 420.

Referring to FIGS. 11A and 11A-1, in one embodiment, the implant 420 desirably includes a dual lumen filling tube 434 having a first conduit 442 adapted to transmit a first solution to a first reservoir 424 of the implant and a second conduit 444 adapted to transmit a second solution to the enclosed space or second reservoir 430 bounded by the porous patch 428. The first conduit 442 desirably extends between a first chamber 454 of an injection dome 440 and the first internal chamber 424 bounded by the implant shell 422.

Referring to FIG. 11A-1, in one embodiment, the injection dome 436 is preferably a dual chamber injection dome including a first chamber 454 adapted to receive a first solution and a second chamber 456 adapted to receive a second solution. The first chamber 454 is preferably in communication with a first coupler 458, which, in turn, is in fluid communication with the first conduit 442 of the filling tube 434. The injection dome 440 also desirably includes a second coupler 464 that provides a second fluid path from the second chamber 456 to the second conduit 444 of the filling tube 434.

Figure 11B:
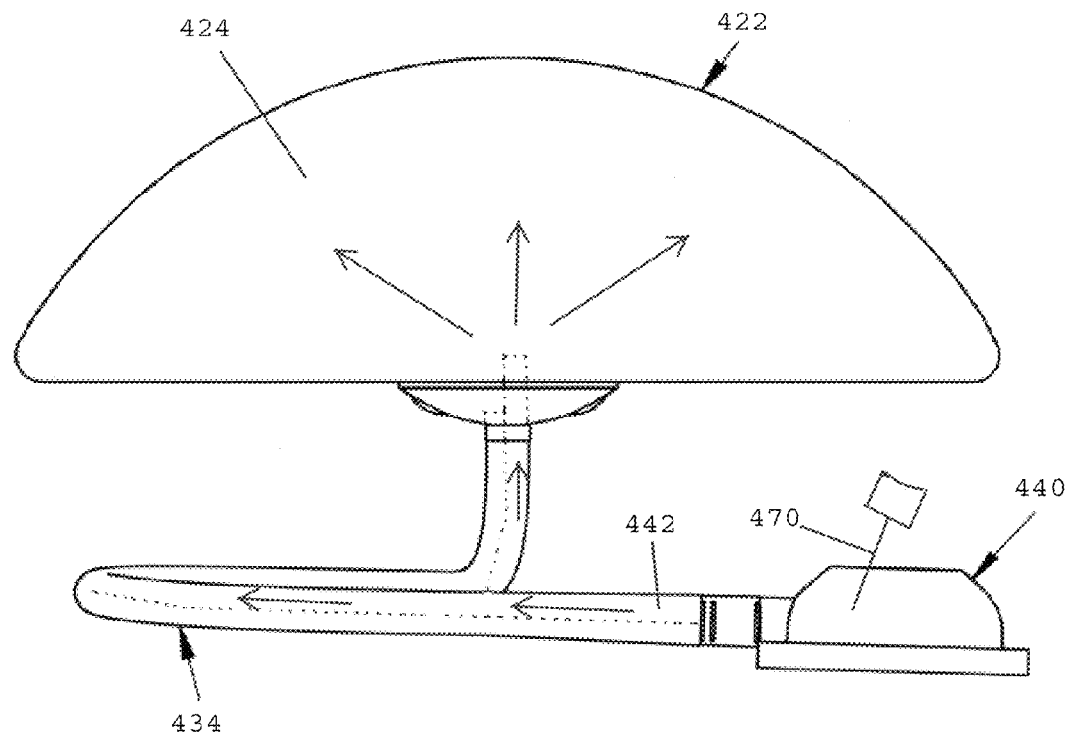
Figures 1, 11B:
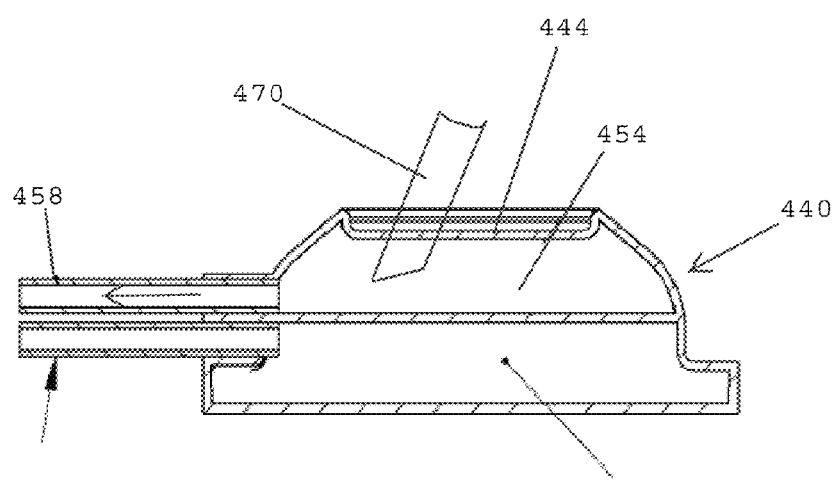

Referring to FIGS. 11B and 11B-1, in one embodiment, it may be desirable to introduce a first solution, such as a saline solution, into the first reservoir 424 of the implant shell 422. In one embodiment, an injection needle 470 is advanced through the injection cover 444 of the injection dome so that a distal end of the injection needle is located within the first chamber 454 of the injection dome 440. A plunger on a syringe may be depressed for injecting the first solution into the second chamber 454. The first solution preferably passes through the first coupler 458 and into the first conduit 442 of the filling tube 434. The first solution is preferably dispensed from the distal end of the first conduit 442 and into the first reservoir 424 for expanding the size or increasing the firmness of the silicone shell 422.

Figure 11C:
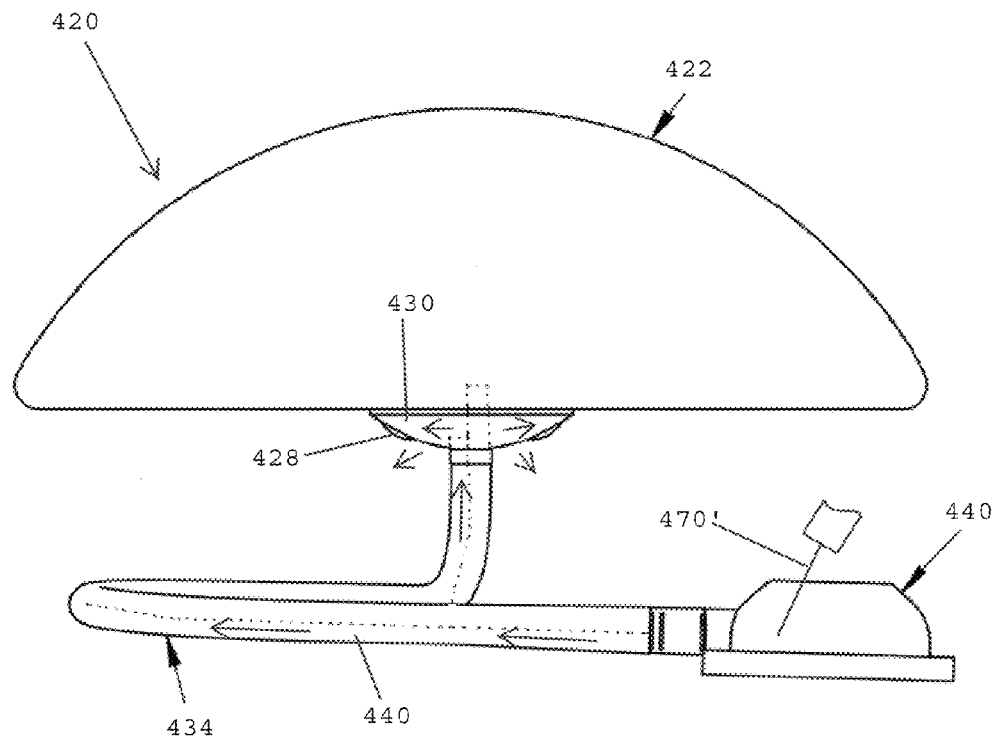
Figures 1, 11C:
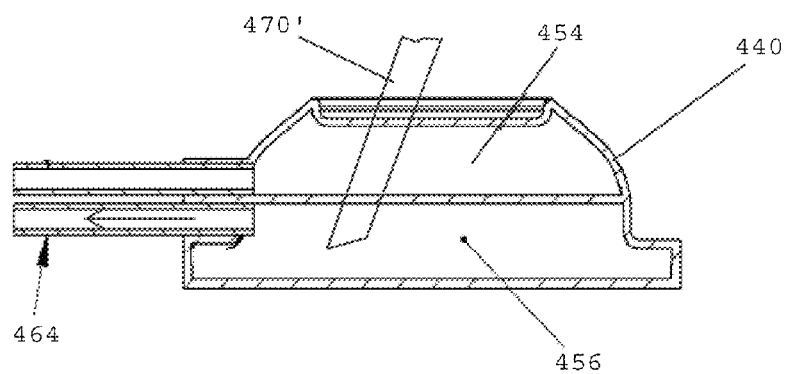

Referring to FIGS. 11C and 11C-1, in one embodiment, it may be desirable to introduce a second solution, such as a drug solution, into the implant 420 so that it may be diffused into the tissue surrounding the implant. In one embodiment, a second injection needle 470', preferably containing the second solution, is advanced into the second chamber 456 of the injection dome 440. A plunger on a syringe may be depressed for dispensing the second solution into the second chamber 456. The second solution preferably advances through the second coupler 464 of the injection dome 440 and into the second conduit 444 of the filling tube 434. The second solution is preferably dispensed from a distal end of the second conduit 444 into the second reservoir 430 defined by the patch 428. The patch 428, such as a silicone patch, is desirably porous so that the second solution disposed therein may diffuse over time into the tissue surrounding the implant 420. The number and size of the pores provided on the patch 430 may be modified for controlling the diffusion rate of the second solution into the surrounding tissue.

In one embodiment, medical personnel may preferably re-use the injection dome 440 many times for adding additional solution into the respective reservoirs 424, 430 defined by the implant shell 422 and the patch 428, respectively. As a result, medical personnel may re-charge or re-fill the internal reservoirs 424, 430, as necessary to enhance therapeutic benefit. In one embodiment, the second solution is a drug solution, such as an antibiotic or anti-fungal solution, that enhances acceptance and retention of the expandable implant 420. Additional doses of the drug solution may be repeatedly injected into the implant to facilitate patient acceptance of the implant 420.

Figure 12A:
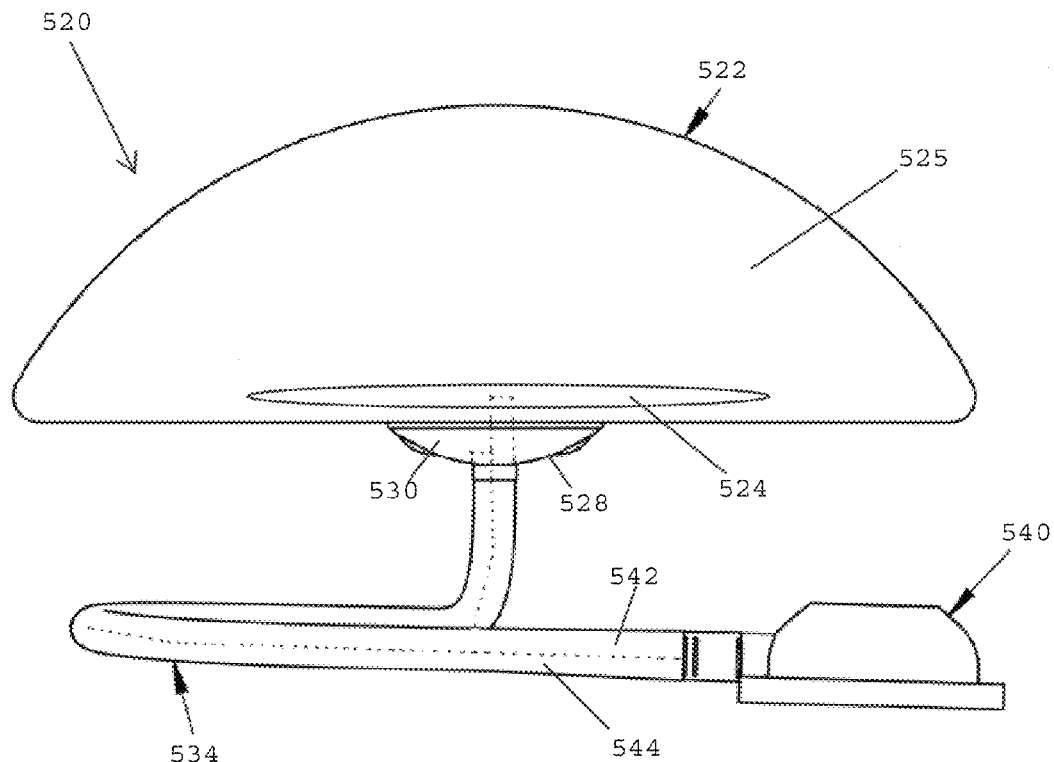
FIGS. 12A-12C show a method of filling an expandable implant using an injection dome, in accordance with one embodiment of the present invention.
Figures 1, 12A:
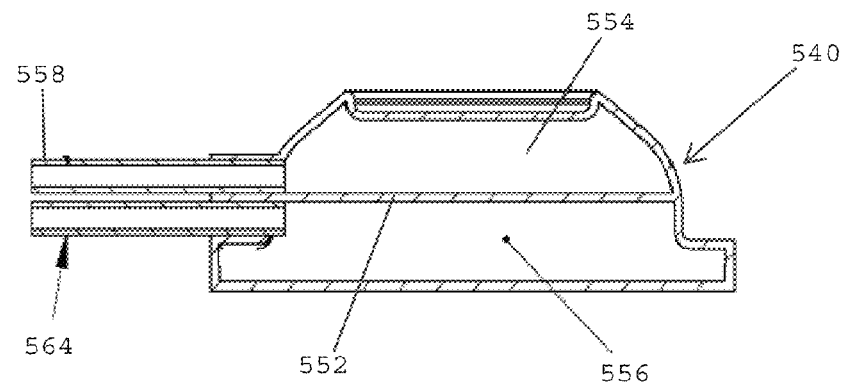

Referring to FIG. 12A, in one embodiment, an implant 520 includes an implant shell 522 that is filled with a silicone gel 525 to a predetermined volume. In one embodiment, the gel-filled implant 520 preferably includes the implant shell 522 that defines an outer surface of the implant. The implant shell 522 is filled with the silicone gel 525. The implant 520 includes a first internal reservoir 524 that is adapted to be filled with a saline solution for expanding the implant.

In one embodiment, the implant preferably includes a patch 528, such as a silicone patch, that covers at least a portion of the posterior face 532 of the implant 520. The patch 528 desirably includes a porous membrane so that a solution placed within a second reservoir 530 defined by the patch may diffuse through the porous membrane and into tissue surrounding the implant 520.

Referring to FIGS. 12A and 12A-1, in one embodiment, the implant 520 is desirably coupled with a dual chamber injection dome 540 including a first chamber 554 and a second chamber 556. The first and second chambers are desirably divided by a diaphragm 552 that preferably prevents mixing of solutions injected into the respective first and second chambers 554, 552. The implant desirably includes a dual lumen filling tube 534 having a first conduit 542 extending between the injection dome 540 and the first reservoir 524 surrounded by the silicone gel 525. The dual lumen filling tube 534 also desirably includes a second conduit 544 that provides a second fluid passageway between the injection dome 540 and the second reservoir 530 bounded by the patch 528.

In one embodiment, a first solution, such as a saline solution, introduced into a first chamber 554 of the injection dome 540 desirably passes through a first injection dome coupler 558, through the first conduit 542 of the filling tube 534, and into the first reservoir 524 located within the implant shell 522. As the first solution is introduced into the first reservoir 524, the implant 520 may grow in size and/or become firmer.

A second solution introduced into a second chamber 556 of the injection dome 540 desirably passes through a second injection dome coupler 564, through the second conduit 544 of the filling tube 534, and into the second reservoir 530 bounded by the patch 528. The divider 552 within the injection dome 540 preferably extends between the first and second chambers 554, 556 for separating solutions in the respective chambers 554, 556 from one another, if necessary.

Figure 12B:
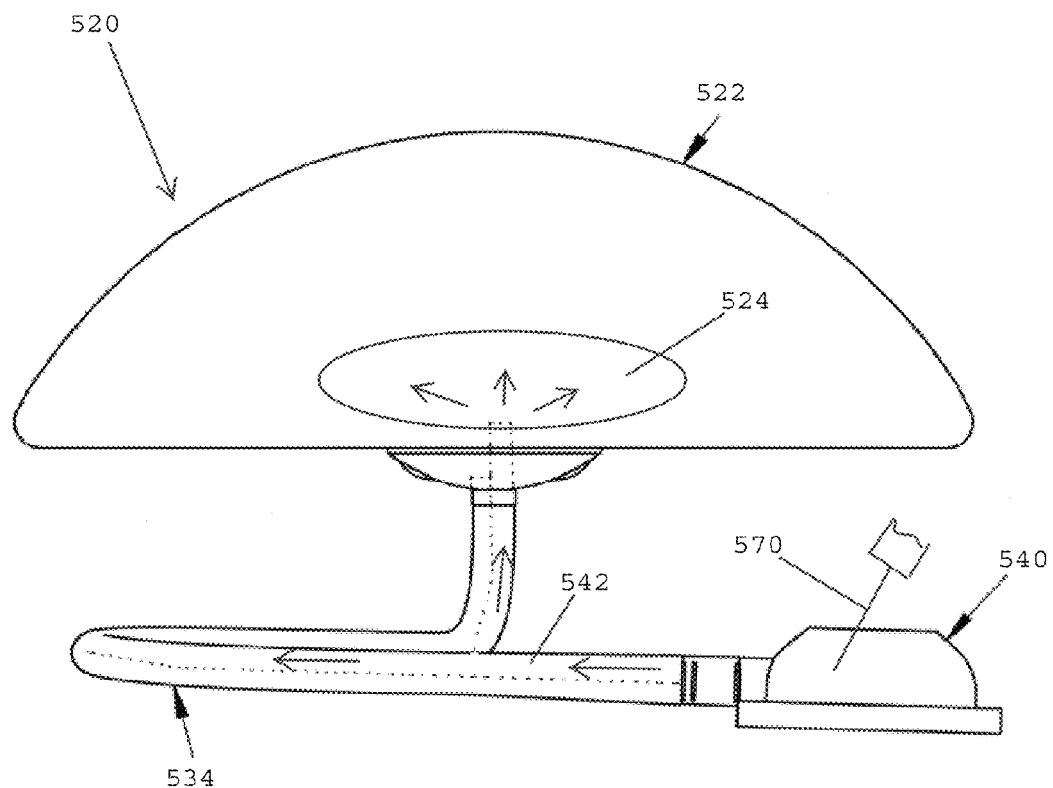
Figures 1, 12B:
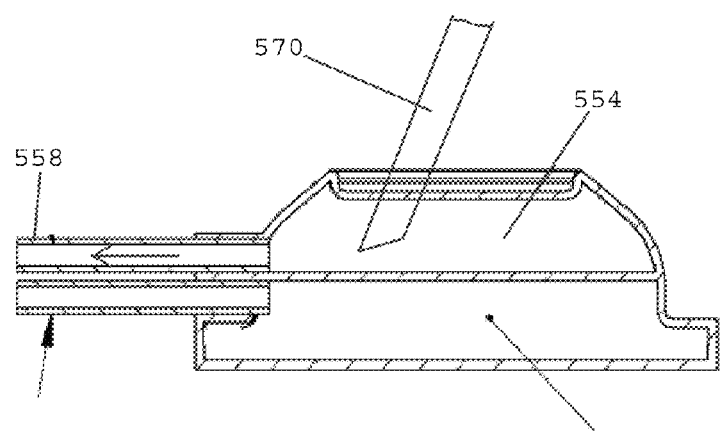

Referring to FIGS. 12B and 12B-1, in one embodiment, a first injection needle 570 is advanced into the first chamber 554 for introducing a first solution therein. A plunger on a syringe may be depressed for dispensing the first solution from the injection needle 570. The dispensed solution passes from the first chamber 554, into the first injection dome coupler 558, and into the first filling tube conduit 542. The solution continues downstream until it reaches a distal end of the first conduit 542 for being dispensed into the first reservoir 524. As the first solution is dispensed within the first reservoir 524, the size of the first reservoir 524 increases, which, in turn, increases the size and/or firmness of the implant shell 522. Medical personnel may introduce additional doses of the first solution for increasing the size of the implant 520 until it reaches a desirable size. Medical personnel may also withdraw the first solution from the first reservoir 524 by reversing the above-described process.

Figure 12C:
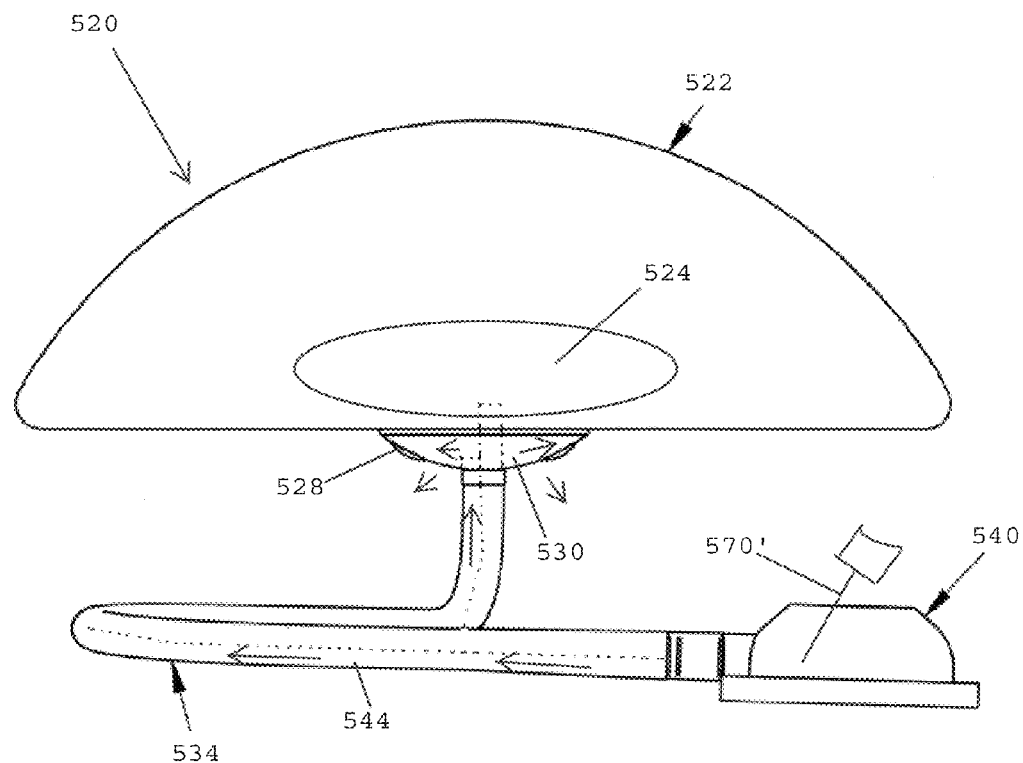
Figures 1, 12C:
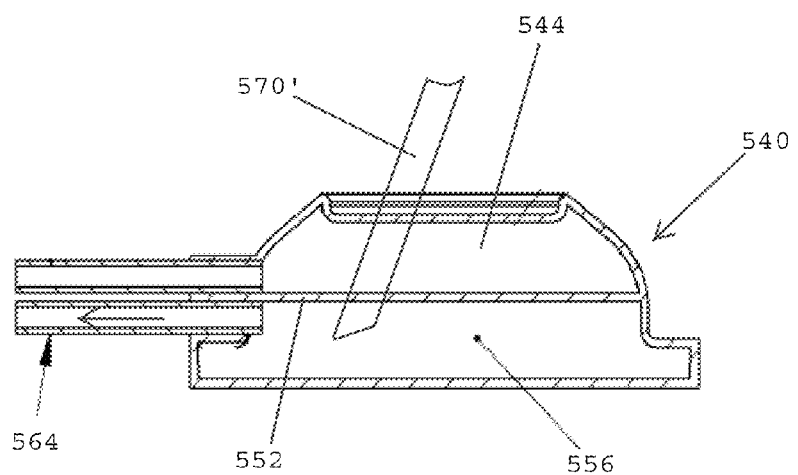

Referring to FIGS. 12C and 12C-1, in one embodiment, it may be desirable to introduce a second solution, such as a drug solution, into the implant 520. In one embodiment, a second injection needle 570' is advanced into the injection dome 540 so that the injection needle pierces the injection cover 544 and the divider diaphragm 552, and the distal end of the injection needle 570' reaches the second chamber 556 of the injection dome 540. A plunger on a syringe may be depressed for introducing the second solution into the second chamber 556 of the injection dome 540. The second solution then desirably passes through the second injection dome coupler 564 and the second filling tube conduit 544 of the filling tube 534. The second solution desirably continues downstream until it is dispensed within the second reservoir 530 bounded by the porous patch 528. The patch 528 is preferably porous so that the second solution disposed within second reservoir 530 preferably diffuses though the patch and into the tissue surrounding the implant 520. The exact porosity of the patch 530 may be modified to provide for different diffusion rates. Medical personnel may dispense additional doses of the second solution into the implant as necessary to facilitate the patient's acceptance and retention of the implant. In one embodiment, medical personnel may introduce a first dose of the second solution at a first date, and wait a period of time before introducing one or more additional doses. In one embodiment, a patient may re-visit medical personnel so that the medical personnel may introduce additional doses of the second solution at the follow-up visits. In one embodiment, medical personnel may continue to introduce the second solution into the implant 520 until the medical personnel are confident that the implant has been accepted by the patient's body and that no infections or other problems will occur. The first solution may also be added or removed from the first reservoir 524 to change the size of the implant 520, as necessary.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A breast implant comprising:
    an implant shell including a first fluid reservoir;
    a porous membrane covering an outer surface of said implant shell for defining a second fluid reservoir that is distinct from said first fluid reservoir;
    a filling tube having a first conduit in communication with said first fluid reservoir chamber and a second conduit in communication with said second fluid reservoir;
    an injection dome coupled with said filling tube, said injection dome including a first chamber in communication with said first conduit for supplying a first solution to said first fluid reservoir of said implant, a second chamber in communication with said second conduit for supplying a second solution to said second fluid reservoir, and a diaphragm separating said first and second chambers from one another;
    wherein said injection dome comprises:
        an upper end including an injection cover;
        a lower end including a support base; said first chamber being located adjacent said injection cover;
        said second chamber being located between said support base and said first chamber;
        and said diaphragm extending between said first and second chambers substantially parallel to said support base.

2. The breast implant as claimed in claim 1, wherein said injection cover is pierceable by an injection needle for introducing said first solution into said first chamber, and said diaphragm is pierceable by an injection needle for introducing a second solution into said second chamber, and wherein said injection cover and said diaphragm are adapted to seal holes formed by said injection needles when said injection needles are withdrawn from said injection cover and said diaphragm.

3. The breast implant as claimed in claim 1, wherein said support base has a bottom surface comprising metal.

4. The breast implant as claimed in claim 1, wherein said first solution comprises saline solution and said second solution comprises a drug solution.

* * * * *